(12) United States Patent
Wang et al.

(10) Patent No.: US 9,926,303 B2
(45) Date of Patent: Mar. 27, 2018

(54) PROCESSES OF SYNTHESIZING DIHYDROPYRIDOPHTHALAZINONE DERIVATIVES

(71) Applicant: Medivation Technologies LLC, San Francisco, CA (US)

(72) Inventors: Bing Wang, San Jose, CA (US); Daniel Chu, Santa Clara, CA (US); Yongbo Liu, Shanghai (CN); Quan Jiang, Shanghai (CN); Lei Lu, Ningbo (CN)

(73) Assignee: Medivation Technologies LLC, San Francisco, CA (US)

( * ) Notice: Subject to any disclaimer, the term of this patent is extended or adjusted under 35 U.S.C. 154(b) by 0 days.

(21) Appl. No.: 14/293,642

(22) Filed: Jun. 2, 2014

(65) Prior Publication Data

US 2014/0323725 A1 Oct. 30, 2014

Related U.S. Application Data

(62) Division of application No. 13/023,140, filed on Feb. 8, 2011, now Pat. No. 8,765,945.

(60) Provisional application No. 61/302,457, filed on Feb. 8, 2010.

(51) Int. Cl.
| | | |
|---|---|---|
| *C07D 405/06* | (2006.01) | |
| *C07D 249/08* | (2006.01) | |
| *C07D 401/04* | (2006.01) | |
| *C07D 403/06* | (2006.01) | |
| *C07D 471/06* | (2006.01) | |

(52) U.S. Cl.
CPC ......... *C07D 405/06* (2013.01); *C07D 249/08* (2013.01); *C07D 401/04* (2013.01); *C07D 403/06* (2013.01); *C07D 471/06* (2013.01)

(58) Field of Classification Search
CPC .................................................. C07D 249/08
USPC ....................................... 548/268.8; 544/238
See application file for complete search history.

(56) References Cited

U.S. PATENT DOCUMENTS

| | | | |
|---|---|---|---|
| 4,415,504 A | 11/1983 | Chibata et al. | |
| 4,526,894 A | 7/1985 | Enomoto et al. | |
| 5,328,905 A | 7/1994 | Hamminga et al. | |
| 6,903,098 B1 | 6/2005 | Lubisch et al. | |
| 7,268,138 B2 | 9/2007 | Kalish et al. | |
| 7,429,598 B2 | 9/2008 | Bernardelli et al. | |
| 7,446,117 B2 | 11/2008 | Beswick et al. | |
| 7,456,178 B2 | 11/2008 | Kalish et al. | |
| 7,601,719 B2 | 10/2009 | Kalish et al. | |
| 7,750,008 B2 | 7/2010 | Kalish et al. | |
| 8,012,976 B2 | 9/2011 | Wang et al. | |
| 8,088,760 B2 | 1/2012 | Chu et al. | |
| 8,134,007 B2 | 3/2012 | Bagal et al. | |
| 8,420,650 B2 | 4/2013 | Wang et al. | |
| 8,541,403 B2 | 9/2013 | Chu et al. | |
| 8,735,392 B2 | 5/2014 | Wang et al. | |
| 8,765,945 B2 | 7/2014 | Wang et al. | |
| 8,999,987 B2 | 4/2015 | Wang et al. | |
| 9,018,201 B2 | 4/2015 | Chu et al. | |
| 2004/0106631 A1 | 6/2004 | Bernardelli et al. | |
| 2005/0085476 A1 | 4/2005 | Seko et al. | |
| 2006/0004028 A1 | 1/2006 | Shiromizu et al. | |
| 2008/0058325 A1 | 3/2008 | Kalish et al. | |
| 2009/0088407 A1 | 4/2009 | Kalish et al. | |
| 2009/0318436 A1 | 12/2009 | Albrecht et al. | |
| 2010/0035883 A1 | 2/2010 | Wang et al. | |
| 2011/0027226 A1 | 3/2011 | Vennemann et al. | |
| 2011/0190266 A1 | 8/2011 | Chu et al. | |
| 2011/0190288 A1 | 8/2011 | Chu et al. | |
| 2011/0196153 A1 | 8/2011 | Wang et al. | |
| 2011/0237581 A1 | 9/2011 | Wang et al. | |
| 2011/0301350 A1 | 12/2011 | Pfrengle et al. | |
| 2012/0129865 A1 | 5/2012 | Wang et al. | |
| 2013/0053365 A1 | 2/2013 | Wang et al. | |
| 2013/0190306 A1 | 7/2013 | Wang et al. | |
| 2014/0228369 A1 | 8/2014 | Wang et al. | |
| 2014/0323725 A1 | 10/2014 | Want et al. | |
| 2015/0209357 A1 | 7/2015 | Wang et al. | |
| 2015/0209363 A1 | 7/2015 | Chu et al. | |
| 2016/0280691 A1 | 9/2016 | Henderson | |
| 2017/0217921 A1 | 8/2017 | Henderson et al. | |

FOREIGN PATENT DOCUMENTS

| | | |
|---|---|---|
| DE | 19727410 A1 | 1/1999 |
| EP | 0 848 000 A1 | 6/1998 |
| EP | 0927718 A1 | 7/1999 |
| EP | 1340819 A1 | 9/2003 |
| EP | 2326650 B1 | 2/2014 |
| JP | 2001-302669 A | 10/2001 |
| JP | 2002-284699 A | 10/2002 |
| JP | 2007-505161 A | 3/2007 |
| JP | 2011-530513 A | 12/2011 |
| WO | 96/29327 A1 | 9/1996 |

(Continued)

OTHER PUBLICATIONS

International Searching Authority, "International Search Report and Written Opinion for International Patent Application No. PCT/US2009/051879," (Apr. 2, 2010).

(Continued)

*Primary Examiner* — Paul V Ward

(74) *Attorney, Agent, or Firm* — Morrison & Foerster LLP

(57) ABSTRACT

Provided herein are processes for synthesizing dihydropyridophthalazinone derivatives, such as for example, 5-fluoro-8-(4-fluorophenyl)-9-(1-methyl-1H-1,2,4-triazol-5-yl)-8,9-dihydro-2H-pyrido[4,3,2-de]phthalazin-3(7H)-one and its stereoisomers, which are potent poly(ADP-ribose)polymerase (PARP) inhibitors as well as novel synthetic intermediate compounds.

1 Claim, No Drawings

(56) References Cited

FOREIGN PATENT DOCUMENTS

| WO | 99/11645 A1 | 3/1999 |
|---|---|---|
| WO | 99/59975 A1 | 11/1999 |
| WO | 02/098424 A1 | 12/2002 |
| WO | WO-2003/002567 A1 | 1/2003 |
| WO | 2004/080976 A1 | 3/2004 |
| WO | WO-2004/024691 A1 | 3/2004 |
| WO | 2004/105700 A1 | 12/2004 |
| WO | WO-2005/080356 A1 | 9/2005 |
| WO | WO-2008/001134 A1 | 1/2008 |
| WO | WO-2008/135826 A2 | 11/2008 |
| WO | WO-2008/135826 A3 | 11/2008 |
| WO | 2010/017055 A1 | 2/2010 |
| WO | 2011/097602 A1 | 8/2011 |
| WO | 2011/130661 A1 | 10/2011 |
| WO | WO-2011/140009 A1 | 11/2011 |
| WO | 2012/054698 A1 | 4/2012 |
| WO | 2012/166151 A1 | 12/2012 |
| WO | 2013/028495 A1 | 2/2013 |
| WO | 2011/097334 A1 | 8/2014 |
| WO | WO 2015/069851 A1 | 5/2015 |
| WO | WO-2016/019125 A1 | 2/2016 |

OTHER PUBLICATIONS

International Searching Authority, "Preliminary Report for International Patent Application No. PCT/US2009/051879 ," (Feb. 8, 2011).
International Searching Authority, International Search Report and Written Opinion for International Patent Application No. PCT/US2011/023532 (Apr. 21, 2011).
International Searching Authority, International Search Report and Written Opinion for International Patent Application No. PCT/US2011/023965 (Apr. 18, 2011).
Karlberg et al., "Crystal Structure of the Catalytic Domain of Human PARP2 in Complex with PARP Inhibitor ABT-888," Biochemistry (2010), pp. 1056-1058, vol. 49.
Mendes-Pereira et al., "Synthetic lethal targeting of PTEN mutant cells with PARP inhibitors," EMBO Mol. Med. (2009), pp. 315-322, vol. 1.
Thomas, et al., "Preclinical selection of a novel poly(ADP-ribose) polymerase inhibitor for clinical trial," Mol. Cancer Ther. (2007), pp. 945-956. vol. 6, No. 3.
United Kingdom Intellectual Property Office, "Patents Act 1977 Combined Search and Examination Report under Sections 17 & 18(3) for Application No. GB 0913474.3," (Nov. 12, 2009).
United Kingdom Intellectual Property Office, "Patents Act 1977 Examination Report under Section 18 (3) for Application No. GB 0913474.3," (Sep. 14, 2010).
Stefanska et al., "2, 7-Dihydro-3H-pyridazino[5,4,3-kl]acridin-3-one derivatives, novel type of cytotoxic agents . . . " Biorganic & Medicinal Chemistry (2005), pp. 1969-1975, vol. 3, No. 6.
European Searching Authority, "Supplementary European Search Report for European Patent Application No. EP 11740513.4," (May 29, 2013).
European Searching Authority, "Extended European Search Report for European Patent Application No. 09805360.6," (Feb. 17, 2012).
Merchant et al., "Synthesis of Benzoquinolizine Derivatives," Indian Journal of Chemistry (1987), pp. 471-472, vol. 268.
CAS Reg. No. 1283718-99-9, Chemical Name "5-Quinolinecarboxylic acid, 1 ,2,3,4-tetrahydro-4-oxo-2-(trifluoromethyl)-methyl ester," (Aug. 20, 2012).
International Searching Authority, "International Search Report and Written Opinion for International Patent Application No. PCT/US2011/032728," (Jun. 28, 2011).
Anderson, B.D. and K.P. Flora, "Preparation of Water-Soluble Compounds through Salt Formation," The Practice of Medicinal Chemistry, Weymuth, C.G. (ed.), 1996, Chapter 34, pp. 739-754.
Aveyard et al., "Somatic mutation of PTEN in bladder carcinoma," British Journal of Cancer, (1996), pp. 904-908, vol. 80, issue 5/6.
Bastin, R.J. et al. "Salt Selection and Optimisation Procedures for Pharmaceutical New Chemical Entities," Org. Process Res. Dev. 2000, 4(5), 427-435.
Bauer, J.F., "Polymorphism—A Critical Consideration in Pharmaceutical Development, Manufacturing, and Stability," Journal of Validation Technology, 2008, 15-23.
Berge, S.M. et al., "Pharmaceutical Salts," J. Pharm. Sci. 1977, 66(1), 1-19.
Bruni et al., "PTEN expression is reduced in a subset of sporadic thyroid carcinomas: evidence that PTEN-growth suppressing activity in thyroid cancer cells is mediated by p27KIP1," Oncogene, (2000), pp. 3146-3155, vol. 19.
Cantley et al., "New insights into tumor suppression: PTEN suppresses tumor formation by restraining the phosphoinositide 3-kinase/AKT pathway," Proc. Natl. Acad. Sci., (Apr. 1999), pp. 4240-4245, vol. 96.
EPO Extended European Search Report dated Jul. 3, 2013 for EP Application No. 11740322.0 (5 pages).
EPO Extended European Search Report dated Jul. 10, 2014 for EP Application No. 14154664.8 (7 pages).
Gaymes et al., "Inhibitors of poly ADP-ribose polymerase (PARP) induce apoptosis of myeloid leukemic cells: potential for therapy of myeloid leukemia and myelodysplastic syndromes," Haematologica, (2009), pp. 638-646, vol. 94, No. 5.
Gaymes, et al., "Microsatellite Instability (MSI) in High Risk Myelodyplastic Syndrome (MDS) and Acute Myeloid Leukemia (AML) Cells Promotes Frameshift Mutations in DNA Repair Genes: Indications for PARP Inhibitor Therapy," Blood $52^{nd}$ Annual Meeting of the American Society of Hematology (ASH), (2010), p. 513, vol. 116, No. 21, Abstract 1194, American Society of Hematology, Orlando, FL, USA.
Ham et al., "Impairment of double-strand breaks repair and aberrant splicing of ATM and MRE11 in Leukemia-lymphoma cell lines with microsatellite instability," Cancer Science, (2006), pp. 226-234, vol. 97, No. 3.
ISA, International Search Report and Written Opinion for International Application No. PCT/US2011/057039 dated Nov. 30, 2011 (9 pages).
ISA, International Search Report and Written Opinion for International Application No. PCT/US2011/039045 dated Apr. 27, 2012 (20 pages).
Kurasawa et al., "PTEN expression and methylation status in oral squamous cell carcinoma," Oncology Reports, (2008), pp. 1429-1434, vol. 19.
Mcellin et al., "PTEN Loss Compromises Homologous Recombination Repair in Astrocytes: Implications for Gliobastoma Therapy with Temozolomide or Poly (ADP-Ribose) Polymerase Inhibitors," Cancer Res., (2010), pp. 5457-5464, vol. 70.
McMahon, Gerald, "VEGF Receptor Signaling in Tumor Angiogenesis," The Oncologist, (2000), pp. 3-10, vol. 5, No. 1.
Mriouah et al., "Celluar response to cetuximab in PTEN-silenced head and neck squamous cell carcinoma cell line", International Journal of Oncology, (2010), pp. 1555-1563, vol. 37.
Pinedo et al. "Translational Research: The Role of VEGF in Tumor Angiogenesis," The Oncologist, (2000), pp. 1-2, vol. 5, No. 1.
Salmena et al., "Tenets of PTEN Tumor Suppression," Cell, (May 2, 2008), pp. 403-414, vol. 133.
Science IP Search dated Jan. 9, 2009, 5 pages.
Translation of Office Action for Japanese Application No. 2013-535079, including Japanese language copies of cited references (a) Takada, N., "API form screening and selection in drug discovery stage," Pharm. Stage. 2007, 6(1), 20-25; and (b) Kojima, T., "Optimization of Solid Form Selection in Drug Development," J. Pharm. Sci. Technol., 2008, 68(5), 344-349 (20 pages).
Non-Final Office Action dated Sep. 6, 2013, for U.S. Appl. No. 13/023,140 , filed Feb. 8, 2011, 8 pages.
Diaz, J.L. et al. (2013). "Synthesis and Biological Evaluation of a New Series of Hexahydro-2H-pyrano[3,2-c]quinolines as Novel Selective σ1 Receptor Ligands," J. Med. Chem. 56:3656-3665.
International Search Report dated Oct. 20, 2015, for PCT Patent Application No. PCT/US2015/042867 filed on Jul. 30, 2015, 3 pages.

(56) References Cited

OTHER PUBLICATIONS

International Search Report dated Jan. 23, 2015, for PCT Patent Application No. PCT/US2014/064273 filed on Nov. 6, 2014, 4 pages.
Ivanova, N. V. et al. (2006). "A Convenient Synthesis of 4,5-Disubstituted 1,2,4-Triazoles Functionalized in Position 3," *Synthesis* 2006(1):156-160.
Zips D. et al. (2005). "New Anticancer Agents: In Vitro and In Vivo Evaluation," *In Vivo* 19(1):1-7.
Stefanska, B. et al. (2005). "2,7-Dihydro-3H-Pyridazino[5,4,3-kl]Acridin-3-One Derivatives, Novel Type of Cytrotoxic Agents Active on Multidrug-Resistant Cell Lines. Synthesis and Biological Evaluation," *Bioorganic & Medicinal Chemistry* 13:1969-1975.

PROCESSES OF SYNTHESIZING DIHYDROPYRIDOPHTHALAZINONE DERIVATIVES

CROSS REFERENCE TO RELATED APPLICATIONS

This application is a divisional application of U.S. application Ser. No. 13/023,140, filed Feb. 8, 2011, which claims the benefit of U.S. Provisional application Ser. No. 61/302,457, filed Feb. 8, 2010, all of which applications are herein incorporated by reference in their entireties.

FIELD OF THE INVENTION

The present application discloses improved processes for synthesizing dihydropyridophthalazinone derivatives, such as for example, 5-fluoro-8-(4-fluorophenyl)-9-(1-methyl-1H-1,2,4-triazol-5-yl)-8,9-dihydro-2H-pyrido[4,3,2-de]phthalazin-3(7H)-one and its stereoisomers, which is a potent poly(ADP-ribose)polymerase (PARP) inhibitor, and novel synthetic intermediate compounds.

BACKGROUND OF THE INVENTION

The family of poly(ADP-ribose)polymerases (PARP) includes approximately 18 proteins, which all display a certain level of homology in their catalytic domain but differ in their cellular functions (Ame et al., *BioEssays.*, 26(8), 882-893 (2004)). PARP-1 and PARP-2 are unique members of the family, in that their catalytic activities are stimulated by the occurrence of DNA strand breaks.

PARP has been implicated in the signaling of DNA damage through its ability to recognize and rapidly bind to DNA single or double strand breaks (D'Amours, et al., *Biochem. J.*, 342, 249-268 (1999)). It participates in a variety of DNA-related functions including gene amplification, cell division, differentiation, apoptosis, DNA base excision repair as well as effects on telomere length and chromosome stability (d'Adda di Fagagna, et al., *Nature Gen.*, 23(1), 76-80 (1999)).

Syntheses of dihydropyridophthalazinone derivatives are disclosed in U.S. Patent Publication No. US 2010/0035883 A1, the content of which is hereby incorporated by reference in its entirety. However, the synthetic routes disclosed in US 2010/0035883 A1 present scale-up challenges, inter alia. Accordingly, there exists a need to provide improved synthetic routes to this class of compounds, and particularly for 5-fluoro-8-(4-fluorophenyl)-9-(1-methyl-1H-1,2,4-triazol-5-yl)-8,9-dihydro-2H-pyrido[4,3,2-de]phthalazin-3(7H)-one and its stereoisomers.

SUMMARY OF THE INVENTION

Provided herein are improved synthetic routes and new intermediates that provide scalable and efficient processes for making 5-fluoro-8-(4-fluorophenyl)-9-(1-methyl-1H-1,2,4-triazol-5-yl)-8,9-dihydro-2H-pyrido[4,3,2-de]phthalazin-3(7H)-one, as shown in formula (1), and its enantiomer compounds, as shown in formulas (1a) and (1b):

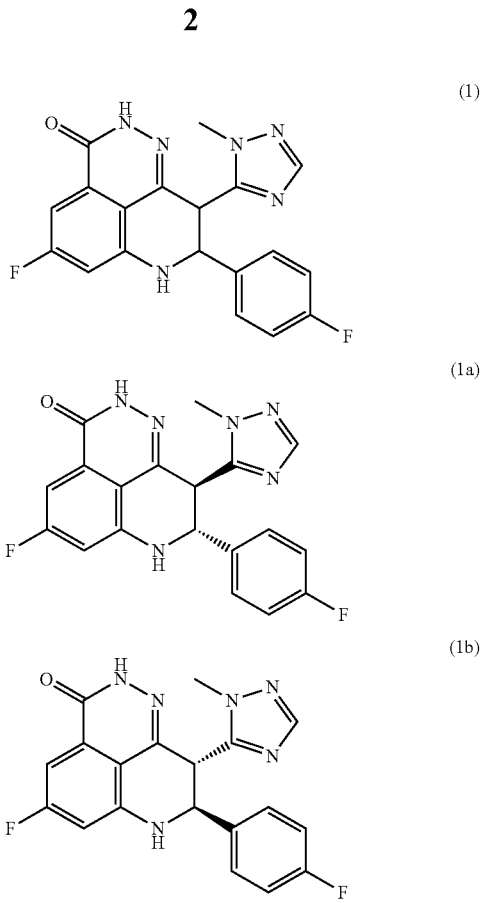

or salts thereof. In particular, the overall yield for the syntheses included herein are improved over the art.

In a first embodiment, the method comprises the following steps:

Step a) reacting a compound of formula (2):

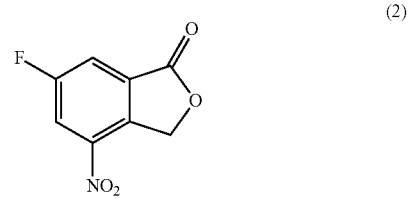 [SMILES: O=C1OCc2c1cc(F)cc2[N+](=O)[O-]]

with 1-methyl-1H-1,2,4-triazole-5-carbaldehyde to produce a compound of formula (3):

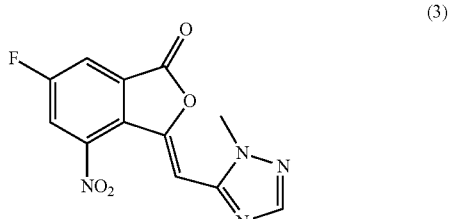

or a salt thereof;

Step b) treating the compound of formula (3) with a lower alkyl alcohol, such as for example, HO—R, where R=$C_1$-$C_4$ alkyl, preferably methanol, to produce a compound of formula (4):

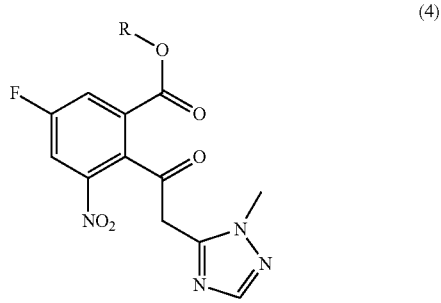
(4)

or a salt thereof;

Step c) reacting the compound of formula (4), or a salt thereof, with 4-fluorobenzaldehyde in the presence of a reducing reagent and an acid or a Lewis acid to produce a compound of formula (5):

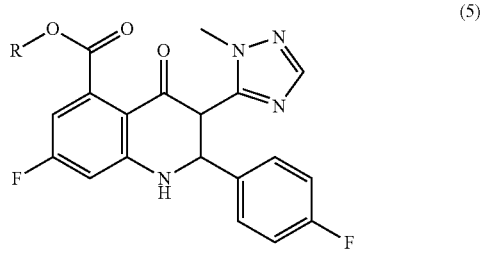
(5)

or a salt thereof;

Step d) performing a separation, for example, a chiral chromatography separation, of the compound of formula (5) to yield two enantiomer compounds of formulas (6a) and (6b):

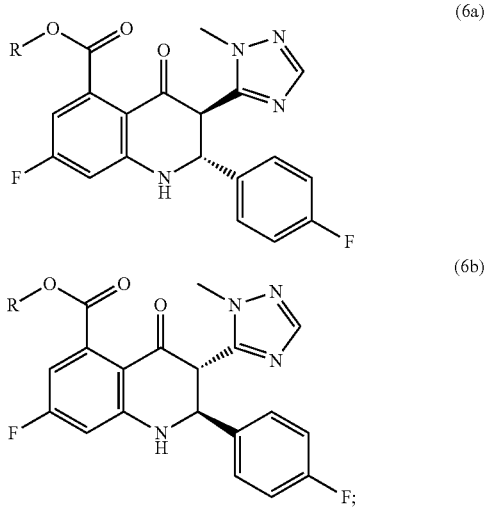
(6a)

(6b)

and

Step e) reacting the enantiomer of formula (6a) or (6b) with hydrazine to obtain the enantiomer of formula (1a) or (1b).

In a second embodiment, the enantiomer of formula (1a) or (1b) is prepared by first treating the compound of formula (5) with hydrazine to afford the racemate of formula (1) and then performing chiral chromatography separation to yield the two enantiomers of formulas (1a) and (1b).

In a third embodiment, an alternative method comprises the following steps:

Step a) reacting the compound of formula (3), or a salt thereof, with hydrazine hydrate to produce a compound of formula (7):

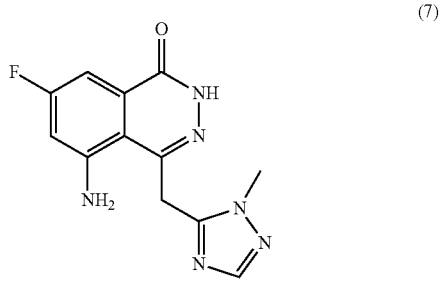 [SMILES: Cn1ncnc1Cc1n[nH]c(=O)c2cc(F)cc(N)c12]
(7)

or a salt thereof;

Step b) reacting the compound of formula (7) with 4-fluorobenzaldehyde in an inert solvent at elevated temperature to produce a compound of formula (8):

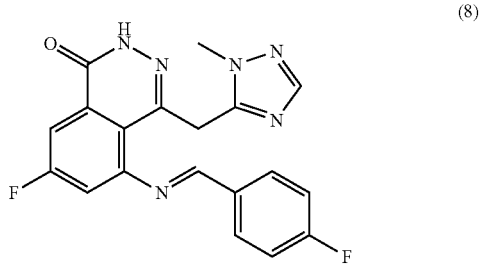 [SMILES: Cn1ncnc1Cc1n[nH]c(=O)c2cc(F)cc(/N=C/c3ccc(F)cc3)c12]
(8)

or a salt thereof;

Step c) treating the compound of formula (8) with a base in an inert solvent to produce the compound of formula (1); and Step d) performing chiral chromatography separation of the compound of formula (1) to yield the two enantiomers of formulas (1a) and (1b).

In the fourth embodiment, yet another alternative method comprises the following steps:

Step a) reacting the compound of formula (4) with 4-fluorobenzaldehyde in the presence of a base, to produce a compound of formula (9):

(9)

[Chemical structure of compound (9)]

or a salt thereof; wherein R is $C_1$-$C_6$ alkyl (lower alkyl).

Step b) reacting the compound of formula (9) with a reducing reagent to produce the compound of formula (5) or a compound of formula (10):

(10)

[Chemical structure of compound (10)]

or a salt thereof, wherein R is $C_1$-$C_6$ alkyl;

Step c) reducing the compound of formula (10) with a reducing reagent to produce the compound of formula (5);

Step d) performing a chiral chromatography separation of the compound of formula (5) to obtain the enantiomers of formulas (6a) and (6b); and Step e) reacting the enantiomer of formula (6a) or (6b) with hydrazine hydrate to produce the enantiomer of formula (1a) or (1b).

In a fifth embodiment, yet another method comprises reacting the compound of formula (9) with hydrazine to produce the compound of formula (1) and separating via chiral chromatography separation to yield the two enantiomers (1a) and (1b).

DETAILED DESCRIPTION OF THE INVENTION

PARP has an essential role in facilitating DNA repair, controlling RNA transcription, mediating cell death, and regulating immune response. PARP inhibitors demonstrate efficacy in numerous models of disease particularly in models of ischemia reperfusion injury, inflammatory disease, degenerative diseases, protection from above adverse effects of cytotoxic compounds, and potentiation of cytotoxic cancer therapy. PARP inhibitors are efficacious in the prevention of ischemia reperfusion injury in models of myocardial infarction, stoke, other neural trauma, organ transplantation, as well as reperfusion of the eye, kidney, gut and skeletal muscle. PARP inhibitors are efficacious in inflammatory diseases such as arthritis, gout, inflammatory bowel disease, CNS inflammation such as MS and allergic encephalitis, sepsis, septic shock, hemorrhagic shock, pulmonary fibrosis, and uveitis. PARP inhibitors also show benefit in several models of degenerative disease including diabetes and Parkinson's disease. PARP inhibitors ameliorate the liver toxicity following acetaminophen overdose, cardiac and kidney toxicities from doxorubicin and platinum based antineoplastic agents, as well as skin damage secondary to sulfur mustards. In various cancer models, PARP inhibitors are shown to potentiate radiation and chemotherapy by increasing apoptosis of cancer cells, limiting tumor growth, decreasing metastasis, and prolonging the survival of tumor-bearing animals.

Provided herein are improved processes and new intermediates for preparing dihydropyridophthalazinone derivatives, and in particular, a compound of formula (1) or its enantiomer compounds of formula (1a) and (1b):

(1)

[Chemical structure of compound (1)]

(1a)

[Chemical structure of compound (1a)]

(1b)

[Chemical structure of compound (1b)]

or their salts thereof.

In one embodiment, provided herein, is a process of making a compound of formula (1), which includes reacting a compound of formula (5):

(5)

[Chemical structure of compound (5)]

or a salt thereof with hydrazine monohydrate. In certain embodiments, the reaction takes place in an inert solvent at a temperature of about 0 to about 140° C. for about 1 to about 24 hours.

In certain embodiments, the inert solvent can include water; an alcohol, such as methanol, ethanol, n-propanol, isopropanol, n-butanol, iso-butanol, tert-butanol, or ethylene glycol; an ether, such as diethyl ether, diisopropyl ether, tetrahydrofuran, 2-methyl-tetrahydrofuran, or dioxane; an amide, such as dimethylformamide or dimethylacetamide; an ester, such as ethyl acetate, methyl acetate, or ethyl formate; a chlorinated hydrocarbon, such as dichloromethane, chloroform, or dichloroethane; a hydrocarbon, such as hexane, heptanes, benzene, toluene, or xylene; or a nitrile, such as acetonitrile; or a combination thereof. In certain embodiments, the solvent is an alcohol. In certain embodiments, the solvent is methanol or ethanol.

In certain embodiments, the reaction temperature can be any value or range between, and including, about 0° C. to about 140° C. For example, in certain embodiments, the reaction temperature can be from about 0° C. to about 25° C.; from about 0° C. to about 100° C.; from about 0 to about 120° C.; from about 20° C. to about 40° C.; from about 25° C. to about 60° C.; from about 100° C. to about 140° C.; or at about 25° C.; at about 40° C.; at about 50° C.; or at about 60° C.

In another embodiment, provided herein, is a process for preparing a compound of formula (5) or a salt thereof, wherein R is $C_1$-$C_6$ alkyl. In certain embodiments, the process includes reacting a compound of formula (4):

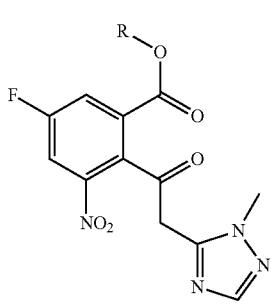

(4)

or a salt thereof with 4-fluorobenzaldehyde in the presence of an acid, or a Lewis acid, and a reducing reagent in an inert solvent at temperature from about 0 to about 80° C. for about 1 to about 5 hours.

In certain embodiments, the acid may be an appropriate inorganic or organic acid. Appropriate inorganic acids include hydrochloric, hydrobromic, hydroiodic, nitric, carbonic, fulfuric, and phosphoric acids. In other embodiments, appropriate organic acids may be selected from aliphatic, cycloaliphatic, aromatic, araliphatic, carboxylic, and sulfonic classes of acids. Examples of these acids include formic, acetic, propionic, succinic, glycolic gluconic, lactic, malic, tartaric, citric, ascorbic, glucuronic, maleic, fumaric, pyruvic, aspartic, glutamic, benzoic, anthranilic, 4-hydroxbenzoic, phenylacetic, mandlic, embonic, methylsulfonic, trifluromethanesulfonic, ethanesulfonic, 2-hydroxyethanesulfonic, amphorsulfonic, benzenesulfonic, pantothenic, trifluoroacetic, p-toluenesulfonic, sulfanilic, cyclohexylaaminosulfonic, stearic, alginic, β-hydroxybutyric, salicylic, galactaric, and galacuronic acids. In certain embodiments, the acid is an inorganic acid. In certain embodiments, the acid is HCl. In other embodiments, the acid is an organic acid. In certain embodiments, the organic acid is acetic acid. In certain embodiments, the organic acid is trifluoroacetic acid. In certain embodiments, the acid is p-toluenesulfonic acid.

In certain embodiments, the Lewis acid is selected from the group consisting of a metal triflate, a metal halide, a metal perchlorate, or a metal tetrafluorobarate. Examples of metal triflates include Li(OTf), Sn(OTf)$_2$, Cu(OTf)$_2$, Bi(OTf)$_3$, Ca(OTf)$_2$, Al(OTf)$_3$, Sm(OTf)$_3$, Yb(OTf)$_3$, and Sc(OTf)$_3$. Examples of metal halides include CeCl$_3$, WCl$_3$, ZrCl$_4$, RuCl$_3$, AlCl$_3$, SbCl$_3$, CoCl$_2$, CdCl$_2$, ZnCl$_2$, TaCl$_5$, InCl$_3$, BiCl$_3$, VCl$_3$, SnCl$_4$, TiCl$_4$, ZrCl$_4$, InBr$_3$, MgBr$_2$, SmI$_2$, and SmCl$_3$. Examples of perchlorates include LiClO$_4$, NaClO$_4$, Zn(ClO$_4$)$_2$, and Cu(ClO$_4$)$_2$. In certain embodiments, the Lewis acid is AlCl$_3$.

In certain embodiments, the reducing reagent is selected from the group consisting of sodium borohydride, sodium cyanoborohydride, powdered Fe, TiCl$_3$, SnCl$_2$, hydrazine, and hydrogen in the presence of a transition metal catalyst. In certain embodiments, the reducing reagent is TiCl$_3$. In certain embodiments, the reducing reagent is powdered Fe. In certain embodiments, the reducing reagent is hydrogen in the presence of a transition metal catalyst. In certain embodiments, the reducing reagent is SnCl$_2$.

In certain embodiments, the transition metal catalyst is selected from the group consisting of palladium, nickel, and platinum.

In another embodiment, provided herein, is a process for preparing a compound of formula (4) or a salt thereof, wherein R is $C_1$-$C_6$ alkyl. In certain embodiments, the process includes reacting a compound of formula (3):

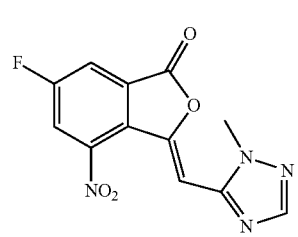

(3)

or a salt therein, with an alcohol either in the presence or absence of an acid at a temperature of about 0 to about 140° C. for about 1 to about 24 hours.

In certain embodiments, the alcohol is selected from the group consisting of lower alkyl alcohols, such as methanol, ethanol, n-propanol, isopropanol, n-butanol, iso-butanol, tert-butanol. In certain embodiments, the alcohol is methanol. In certain embodiments, either an inorganic acid such as HCl and an organic acid such as acetic or trifluoroacetic acids is used. In certain embodiments, an acetic acid is used.

In another embodiment, provided herein, is a process for preparing a compound of formula (3). In certain embodiments, the method includes reacting a compound of formula (2):

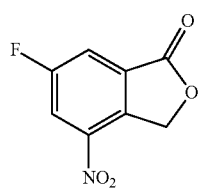

(2)

with 1-methyl-1H-1,2,4-triazole-5-carbaldehyde in the presence of a base and a water scavenger agent in an inert solvent at a temperature from about 0° C. to about 140° C. for about 1 to about 24 hours.

In certain embodiments, the base is selected from either an inorganic base, such as sodium carbonate, potassium carbonate, cesium carbonate, potassium hydride, and sodium hydride; or an organic base, such as trimethylamine, triethylamine, diisopropylethylamine, pyridine, N,N-dimethylaminopyridine, lutidine, imidazole, and piperidine. In certain embodiments, the base is an organic base. In certain embodiments, the base is a triethylamine.

In certain embodiments, the water scavenger is selected from the group consisting of sodium sulfate, magnesium sulfate, molecular sieves, and acid anhydrides. In certain embodiments, the water scavenger is an acetic anhydride.

In another embodiment, provided herein, is a method for making a compound of formula (5). The method comprises carrying out a reaction of a compound of formula (9):

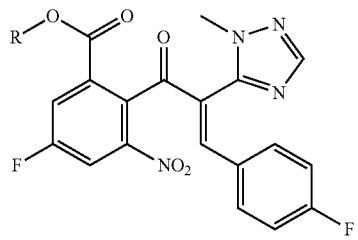

(9)

or a salt thereof in the presence of a reducing reagent in an inert solvent. In certain embodiments, the reducing reagent is powdered Fe. In certain embodiments, the reducing reagent is a sodium borohydride. In certain embodiments, the reducing reagent is hydrogen in the presence of a transition metal catalyst. In certain embodiments, the transition metal catalyst is palladium on carbon.

In certain embodiments, a compound of formula (9) is converted to a compound of formula (10):

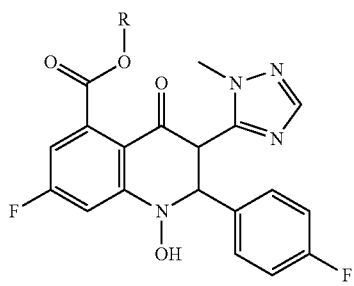

(10)

or a salt thereof, wherein R is $C_1$-$C_6$ alkyl. In this case, the compound of formula (10) is further reduced with a reducing reagent to a compound of formula (5).

In another embodiment, provided herein, is a method for making a compound of formula (9). In certain embodiments, the process comprises reacting a compound of formula (4):

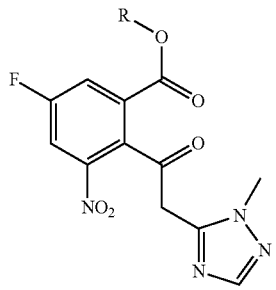

(4)

or a salt thereof, with 1-methyl-1H-1,2,4-triazole-5-carbaldehyde in a inert solvent under aldol condensation dehydration conditions, which include, but are not limited to, using a base selected from lithium alkoxide, sodium alkoxide, lithium diisopropylamine, triethylamine, diisopropylethylamine, piperidine, pyrrolidine, and proline at a temperature of about 0 to about 140° C. for about 1 to about 60 hours. In certain embodiments, the base is an L-proline, and the inert solvent is a mixture of methanol and dichloromethane. In certain embodiments, the solvent is DMSO.

In another embodiment, provided herein, is an alternative method of preparing a compound of formula (1) which includes reacting a compound of formula (8):

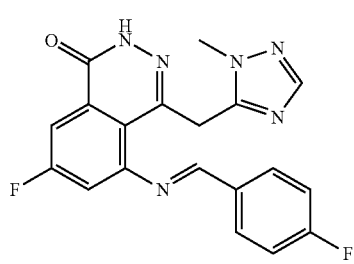

(8)

or a salt thereof with a base in an inert solvent at a temperature from about 0° C. to about 140° C. for about 1 to about 24 hours. In certain embodiments, the base is sodium hydride. In certain embodiments, the base is cesium carbonate, and the solvent is tetrahydrofuran. In certain embodiments, the reaction temperature is about 50 to about 60° C.

In another embodiment, provided herein, is a process for preparing a compound of formula (8) or a salt thereof. In certain embodiments, the method comprises reacting a compound of formula (7):

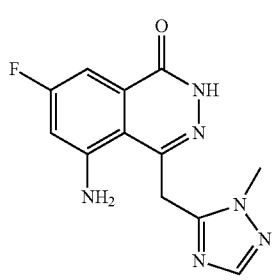

(7)

or a salt thereof with 4-fluorobenzaldehyde in an inert solvent at about 0 to about 140° C. for about 1 to about 48 hours. In certain embodiments, the solvent is acetonitrile.

In another embodiment, provided herein, is a method for preparing a compound of formula (7) or a salt thereof comprising reacting a compound of formula (3):

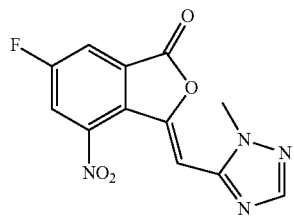

(3)

or a salt thereof with a hydrazine monohydrate in the presence of a acid in an inert solvent at a reaction temperature from about 0 to about 140° C. for about 1 to about 48 hours. In certain embodiments, the solvent is tetrahydrofuran and the acid is acetic acid.

In another embodiment, provided herein, is an alternative method of preparing a compound of formula (1) includes carrying out a reaction of a compound of formula (9):

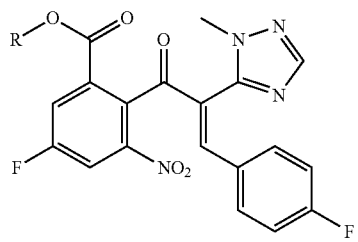

(9)

or a salt thereof, with hydrazine monohydrate in an inert solvent at a temperature of about 0 to about 140° C. for about 1 to about 48 hours. In certain embodiments, the inert solvent is an alcohol. In certain embodiments, the alcohol is methanol.

In another embodiment, provided herein, is a process of making an enantiomer of formula (1a) or (1b) comprising performing a chiral chromatography resolution of a compound of formula (1).

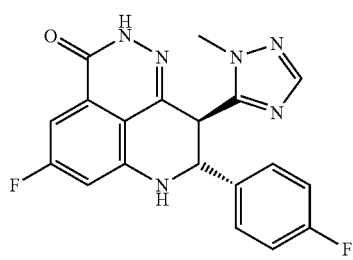

(1a)

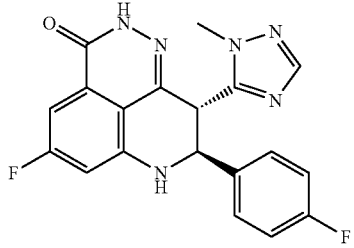

(1b)

In certain embodiments, the chiral chromatography resolution comprises employing preparative HPLC, preparative Supercritical Fluid Chromatography (SFC), or Stimulating Moving Bed chromatography (SMB) on a chiral stationary phase. In certain embodiments, the chiral resolution is achieved by SFC using CHIRALPAK AD or IA column and $CO_2$/MeOH or $CO_2$/EtOH as the mobile phase.

Also provided herein is a process for making an enantiomer of formula (1a) or (1b) comprising treating of an enantiomer of formula (6a) or (6b):

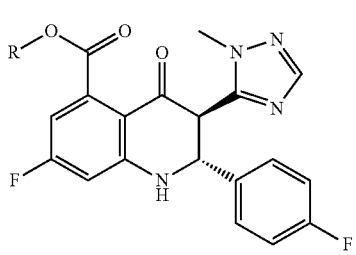

(6a)

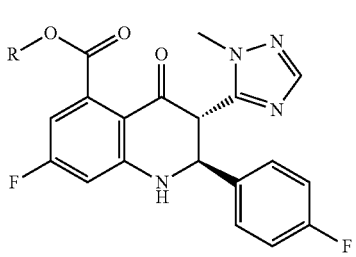

(6b)

with hydrazine monohydrate, wherein R is $C_1$-$C_6$ alkyl. In certain embodiments, the reaction takes place in an inert solvent at a temperature of about 0 to about 140° C. for about 1 to about 24 hours. In certain embodiments, an inert solvent is an alcohol. In certain embodiments, the solvent is methanol or ethanol.

Also provided herein is a method for making an enantiomer of formula (6a) or (6b) comprising resolution of a compound of formula (5) using chiral chromatography resolution:

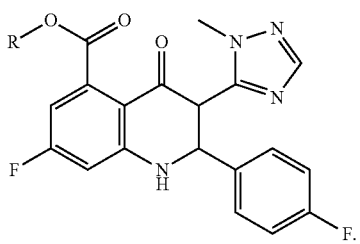

In certain embodiments, chiral chromatography resolution of a compound of formula (5) comprises employing preparative HPLC, preparative Supercritical Fluid Chromatography (SFC), or Stimulating Moving Bed chromatography (SMB) on a chiral stationary phase. In certain embodiments, the chiral resolution is achieved by SFC using CHIRALPAK IC column and $CO_2$/MeOH as the mobile phase. In certain embodiments, chiral resolution is achieved by SMB using CHIRALPAK IC column and acetonitrile as the mobile phase.

EXAMPLES

The following Examples are intended as an illustration of the various embodiments disclosed herein. In certain embodiments, the compounds are prepared by a variety of synthetic routes. These examples are not intended, nor are they to be construed, as limiting the scope of the invention. All publications, patents, and patent applications cited herein are hereby incorporated by reference in their entireties for all purposes.

Example 1

(Z)-6-Fluoro-3-((1-methyl-1H-1,2,4-triazol-5-yl)methylene)-4-nitroisobenzofuran-1(3H)-one (3)

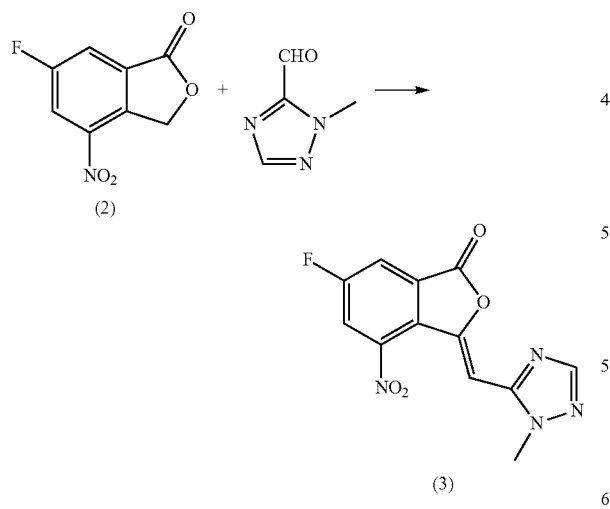

To a 80 L jacketed glass reactor equipped with a chiller, mechanical stirrer, thermocouple, and nitrogen inlet/outlet, at 15-25° C., anhydrous 2-methyl-tetrahydrofuran (22.7 kg), 6-fluoro-4-nitroisobenzofuran-1(3H)-one (2) (2.4 kg, 12.2 mol, 1.00 eq.), and 2-methyl-2H-1,2,4-triazole-3-carbaldehyde (49.6-52.6% concentration in dichloromethane by GC, 3.59-3.38 kg, 16.0 mol, 1.31 eq.) were charged consecutively. Triethylamine (1.50 kg, 14.8 mol, 1.21 eq.) was then charged into the above reaction mixture. The reaction mixture was stirred for another 10 minutes. Acetic anhydride (9.09-9.10 kg, 89.0-89.1 mol, 7.30 eq.) was charged into the above reaction mixture at room temperature for 20-30 minutes. The reaction mixture was heated from ambient to reflux temperatures (85-95° C.) for 80-90 minutes, and the mixture was refluxed for another 70-90 minutes. The reaction mixture was monitored by HPLC, indicating compound (2) was reduced to ≤5%. The resulting slurry was cooled down to 5-15° C. for 150-250 minutes. The slurry was aged at 5-15° C. for another 80-90 minutes. The slurry was filtered, and the wet cake was washed with ethyl acetate (2 L×3). The wet cake was dried under vacuum at 40-50° C. for 8 hours to give 2.65-2.76 kg of (Z)-6-fluoro-3-((1-methyl-1H-1,2,4-triazol-3-yl)methylene)-4-nitroisobenzofuran-1(3H)-one (3) as a yellow solid (2.66 kg, yield: 75.3%, purity: 98.6-98.8% by HPLC). LC-MS (ESI) m/z: 291 (M+1)$^+$. $^1$H-NMR (400 MHz, DMSO-$d_6$) δ (ppm): 3.94 (s, 3H), 7.15 (s, 1H), 8.10 (s, 1H), 8.40-8.42 (dd, $J_1$=6.4 Hz, $J_2$=2.4 Hz, 1H), 8.58-8.61 (dd, $J_1$=8.8 Hz, $J_2$=2.4 Hz, 1H).

Example 2

Methyl 5-fluoro-2-(2-(1-methyl-1H-1,2,4-triazol-5-yl)acetyl)-3-nitrobenzoate (4)

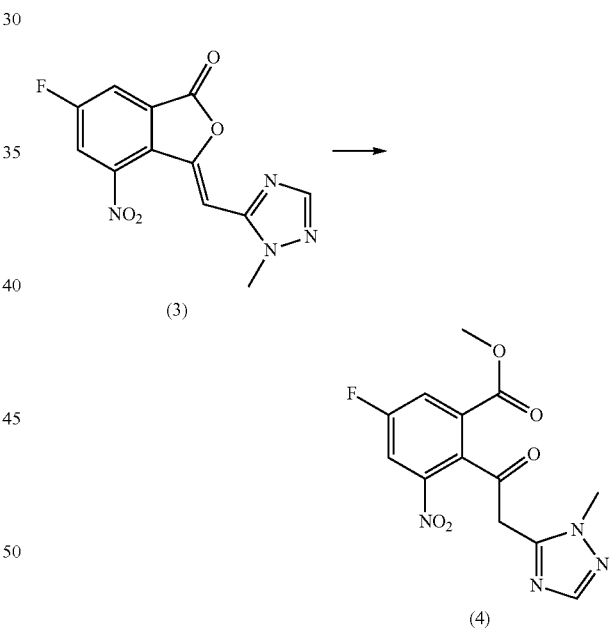

Example 2A (Z)-6-Fluoro-3-((1-methyl-1H-1,2,4-triazol-3-yl)methylene)-4-nitroisobenzofuran-1(3H)-one (3) (177 g, 0.6 mol, 1.0 eq.), and HCl (2 N in methanol, 3 L, 6 mol, 10 eq.) were charged into a 5 L 3-neck flask equipped with mechanical stirrer, thermometer, and nitrogen inlet/outlet. The reaction mixture was stirred at room temperature for 25 hours. The reaction mixture was monitored by HPLC, indicating 0.8% compound (3) remained. The reaction mixture was concentrated under vacuum at 40° C. to dryness, and methyl 5-fluoro-2-(2-(1-methyl-1H-1,2,4-triazol-3-yl)acetyl)-3- nitrobenzoate hydrochloride (4) was obtained as a yellow solid (201 g, yield: 93.4%). It was used for the next step without further purification. LC-MS (ESI) m/z: 323 (M+1)+. $^1$H-NMR (400 MHz, DMSO-d$_6$) δ (ppm): 3.89 (s, 3H), 3.92 (s, 3H), 4.60 (s, 2H), 7.85 (s, 1H), 8.25-8.28 (dd, J$_1$=8.4 Hz, J$_2$=2.8 Hz, 2H), 8.52-8.54 (dd, J$_1$=8.4 Hz, J$_2$=2.8 Hz, 2H).

Example 2B

An alternative workup procedure to that illustrated in Example 2A follows. Instead of evaporating the reaction mixture to dryness, it was condensed to 2 volumes, followed by solvent exchange with 12 volumes of THF, and then 12 volumes of heptane. The slurry mixture was concentrated to 2 volumes and filtered to give the product. As such, 1.8 kilograms of (Z)-6-fluoro-3-((1-methyl-1H-1,2,4-triazol-3-yl)methylene)-4-nitroisobenzofuran-1 (3M-one (3) gave 2.15 kilograms (yield 96.4%) of the product methyl 5-fluoro-2-(2-(1-methyl-1H-1,2,4-triazole-3-yl)acetyl)-3-nitrobenzoate hydrochloride (4).

Example 3

Methyl 7-fluoro-2-(4-fluorophenyl)-3-(1-methyl-1H-1,2,4-triazol-5-yl)-4-oxo-1,2,3,4-tetrahydroquinoline-5-carboxylate (5)

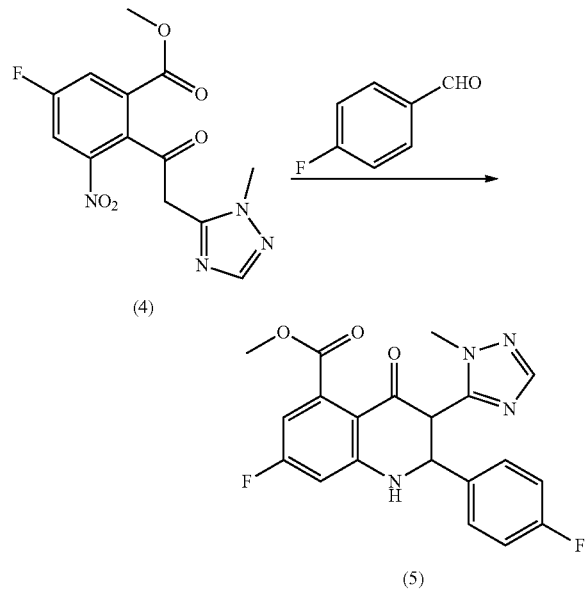

Example 3A

To a suspension of methyl 5-fluoro-2-(2-(1-methyl-1H-1,2,4-triazol-5-yl)acetyl)-3-nitrobenzoate (4) (5 g, 15.5 mmol, 1 eq.) and 4-fluorobenzaldehyde (3.6 g, 29 mmol, 1.87 eq.) in a mixture of solvents tetrahydrofuran (30 mL) and MeOH (5 mL) was added titanium(III) chloride (20% w/w solution in 2N Hydrochloric acid) (80 mL, 6 eq.) dropwise with stirring at room temperature. The reaction mixture was allowed to stir at 30~50° C. for 2 hours. The mixture was then diluted with water (160 mL), and the resulting solution was extracted with ethyl acetate (100 mL×4). The combined organic layers were washed with saturated NaHCO$_3$ (50 mL×3) and aqueous NaHSO$_3$ (100 mL×3), dried by Na$_2$SO$_4$, and concentrated to dryness. This afforded a crude solid, which was washed with petroleum ether (120 mL) to obtain the title compound as a yellow solid (5.9 g, yield: 95%, purity: 97%). LC-MS (ESI) m/z: 399 (M+1)+. $^1$H-NMR (400 MHz, CDCl$_3$) δ (ppm): 3.58 (s, 3H), 3.87 (s, 3H), 4.16-4.19 (d, J2=13.2 Hz, 1H), 4.88 (s, 1H), 5.37-5.40 (d, J2=13.2 Hz, 1H), 6.47-6.53 (m, 2H), 6.97-7.01 (m, 2H), 7.37-7.41 (m, 2H), 7.80 (s, 1H).

Example 3B

An alternative workup procedure to that illustrated in Example 3A follows. After the completion of the reaction, the mixture was extracted with isopropyl acetate (20 volumes×4) without water dilution. The product was isolated by solvent exchange of isopropyl acetate with heptanes followed by re-slurry with MTBE and filtration. As such, 3 kilograms of methyl 5-fluoro-2-(2-(1-methyl-1H-1,2,4-triazol-5-yl)acetyl)-3-nitrobenzoate (4) afforded 2.822 kilograms of the title compound (5) (yield 81%).

Example 3C

To a stirred solution of methyl 5-fluoro-2-(2-(1-methyl-1H-1,2,4-triazol-5-yl)acetyl)-3-nitrobenzoate (4) (580 mg, 2 mmol) and 4-fluorobenzaldehyde (488 mg, 4 mmol) in methanol (0.75 mL) and tetrahydrofuran (4.5 mL) was added concentrated HCl solution (w/w 37%, 6 mL), then reductive powdered Fe (672 mg, 12 mmol) was added slowly to the reaction system. After the addition was complete, the resulting mixture was heated to 60° C. and kept at this temperature for 3 hours. After the disappearance of the starting material (4) as monitored by LC-MS, the reaction mixture was partitioned between ethyl acetate (30 mL) and water (30 mL) and the aqueous phase was extracted with ethyl acetate (20 mL×3). The combined organic phase was dried with Na$_2$SO$_4$, concentrated in vacuo and purified by column chromatography (ethyl acetate:petroleum ether=1:1) to give the title compound (5) as a pale yellow solid (300 mg, yield 40%). LC-MS (ESI) m/z: 399 (M+1)+. $^1$H-NMR (400 MHz, CDCl$_3$) δ (ppm): 3.58 (s, 3H), 3.87 (s, 3H), 4.17 (d, 1H), 4.87 (s, 1H), 5.38 (d, 1H), 6.50 (dd, 2H), 6.99 (dd, 2H), 7.38 (dd, 2H), 7.80 (s, 1H).

Example 3D

To a stirred solution of methyl 5-fluoro-2-(2-(1-methyl-1H-1,2,4-triazol-5-yl)acetyl)-3-nitrobenzoate (4) (580 mg, 2 mmol) and 4-fluorobenzaldehyde (488 mg, 4 mmol) in methanol (0.75 mL) and tetrahydrofuran (4.5 mL) was added SnCl$_2$ (2.28 g, 12 mmol) and concentrated HCl (w/w 37%, 6 mL), the resulting mixture was reacted at 45° C. for 3 hours, until LC-MS indicating the disappearance of the starting material (4) and about 50% formation of the product. The mixture was then partitioned between ethyl acetate (30 mL) and water (30 mL) and the aqueous phase was extracted with ethyl acetate (20 mL×3). The combined organic phase was dried with Na$_2$SO$_4$, concentrated in vacuo and purified by column chromatography (ethyl acetate: petroleum ether=1:1) to give the title compound (5) as a pale yellow solid (10 mg, yield 1.3%). LC-MS (ESI) m/z: 399 (M+1)+. $^1$H-NMR (400 MHz, CDCl$_3$) δ (ppm): 3.58 (s, 3H), 3.87 (s, 3H), 4.17 (d, 1H), 4.87 (s, 1H), 5.38 (d, 1H), 6.50 (dd, 2H), 6.99 (dd, 2H), 7.38 (dd, 2H), 7.80 (s, 1H).

Example 3E

A solution of methyl 5-fluoro-2-(2-(1-methyl-1H-1,2,4-triazol-5-yl)acetyl)-3-nitrobenzoate (4) (580 mg, 2 mmol)

and 4-fluorobenzaldehyde (488 mg, 4 mmol) in methanol (20 mL) and acetic acid (1 mL) was stirred at room temperature for 24 hours under hydrogen (1 barr) in the presence of a catalytic amount of 10% Pd/C (212 mg, 0.2 mmol). After the reaction was complete, the catalyst was removed by filtration through a pad of Celite, the solvent was removed in vacuo, and the residue was purified by column chromatography (ethyl acetate:petroleum ether=1:1) to give the title compound (5) as a pale yellow solid (63 mg, yield 8%). LC-MS (ESI) m/z: 399 (M+1)$^+$. $^1$HNMR (400 MHz, DMSO-$d_6$) δ (ppm): 3.56 (s, 3H), 3.86 (s, 3H), 7.02 (dd, 2H), 7.21 (dd, 2H), 7.90 (s, 1H), 8.08 (s, 1H), 8.26 (dd, 1H), 8.56 (dd, 1H).

Example 4

5-Fluoro-8-(4-fluorophenyl)-9-(1-methyl-1H-1,2,4-triazol-5-yl)-8,9-dihydro-2H-pyrido[4,3,2-de]phthalazin-3(7H)-one (1)

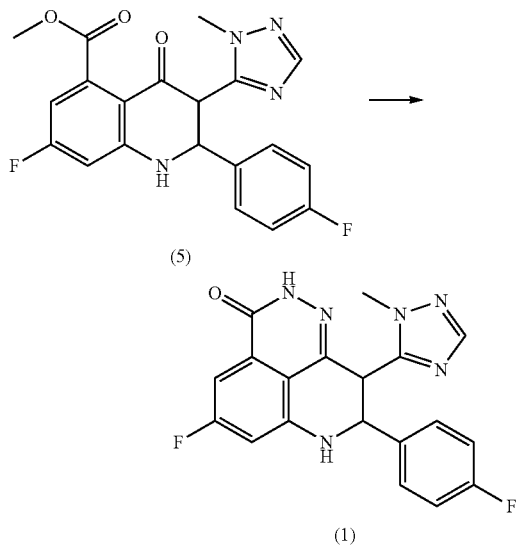

Methyl 7-fluoro-2-(4-fluorophenyl)-3-(1-methyl-1H-1,2,4-triazol-5-yl)-4-oxo-1,2,3,4-tetrahydroquinoline-5-carboxylate (5) (150 g, 0.38 mol, 1.0 eq.) and methanol (1.7 L) were charged into a 3 L 3-neck flask equipped with a mechanical stirrer, thermometer, and nitrogen inlet/outlet. The resulted suspension was stirred at room temperature for 15 minutes. Hydrazine hydrate (85% of purity, 78.1 g, 1.33 mol, 3.5 eq.) was charged dropwise into the above reaction mixture within 30 minutes at ambient temperature. The reaction mixture was stirred at room temperature overnight. The reaction was monitored by HPLC, showing about 2% of compound (5) left. The obtained slurry was filtered. The wet cake was suspended in methanol (2 L) and stirred at room temperature for 3 hours. The above slurry was filtered, and the wet cake was washed with methanol (0.5 L). The wet cake was then dried in vacuum at 45-55° C. for 12 hours. This afforded the title compound as a pale yellow solid (112 g, yield: 78.1%, purity: 95.98% by HPLC). LC-MS (ESI) m/z: 381 (M+1)$^+$. $^1$H-NMR (400 MHz, DMSO-$d_6$) δ (ppm): 3.66 (s, 3H), 4.97-5.04 (m, 2H), 6.91-6.94 (dd, $J_1$=2.4, $J_2$=11.2 Hz, 1H), 7.06-7.09 (dd, $J_1$=2.4, $J_2$=8.8 Hz, 1H), 7.14-7.18 (m, 3H), 7.47-7.51 (m, 2H), 7.72 (s, 1H), 7.80 (s, 1H), 12.35 (s, 1H).

Example 5

5-Amino-7-fluoro-4-((1-methyl-1H-1,2,4-triazol-5-yl)methyl)phthalazin-1(2H)-one

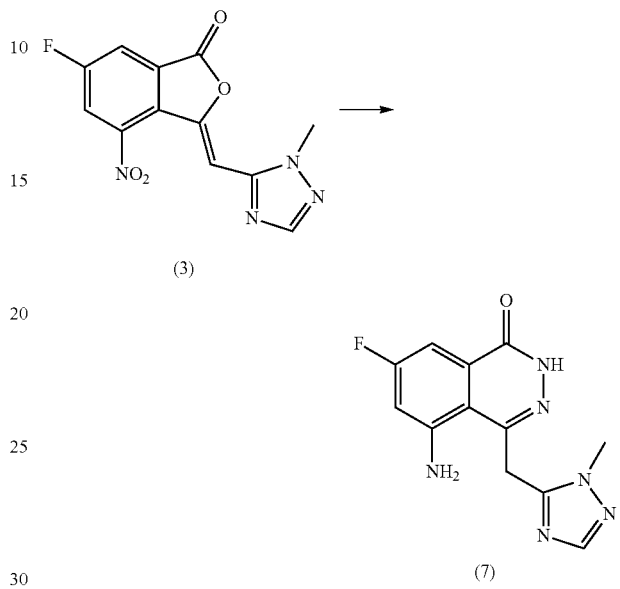

To a solution of 6-fluoro-3-((1-methyl-1H-1,2,4-triazol-3-yl)methylene)-4-nitroiso-benzofuran-1(3H)-one (3) (4.0 g, 135 mmol) in THF (100 mL) was added hydrazine monohydrate (85%) (6 mL) at room temperature under nitrogen atmosphere. The mixture was stirred for 2 hours, then acetic acid (6 mL) was added and the mixture was heated to and kept at 60° C. for 18 hours. The resulting mixture was diluted with water (100 mL) and extracted with ethyl acetate (100 mL×3). The organic layer was dried over anhydrous $Na_2SO_4$ and evaporated to dryness to afford the title compound as a yellow solid (1.6 g, yield 42%). LC-MS (ESI) m/z: 275 (M+1)$^+$.

Example 6

(E)-7-fluoro-5-(4-fluorobenzylideneamino)-4-((1-methyl-1H-1,2,4-triazol-5-yl)methyl)phthalazin-1(2H)-one

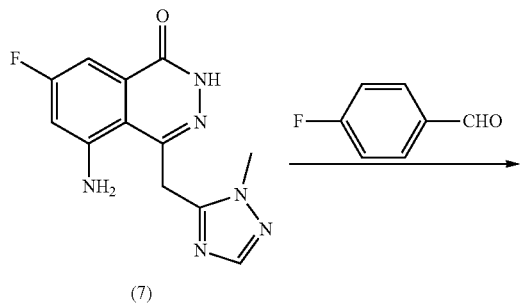

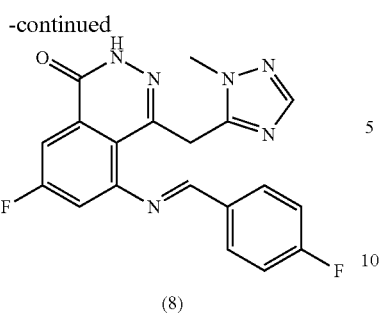

(8)

To a suspended of 5-amino-7-fluoro-4-((1-methyl-1H-1,2,4-triazol-3-yl)methyl) phthalazin-1(2H)-one (7) (1.6 g, 5.8 mmol) in acetonitrile (50 mL) was added 4-fluorobenzaldehyde (2.2 g, 17.5 mmol). The mixture was stirred under reflux under nitrogen for 48 hours. The precipitate was filtered and washed with a mixture of solvents (ethyl acetate/hexane, 1:1, 10 mL). After drying in vacuum, it afforded the title compound as a yellow solid (1.2 g, yield 52%). LC-MS (ESI) m/z: 381 (M+1)$^+$.

Example 7

5-Fluoro-8-(4-fluorophenyl)-9-(1-methyl-1H-1,2,4-triazol-5-yl)-8,9-dihydro-2H-pyrido[4,3,2-de]phthalazin-3(7H)-one (1)

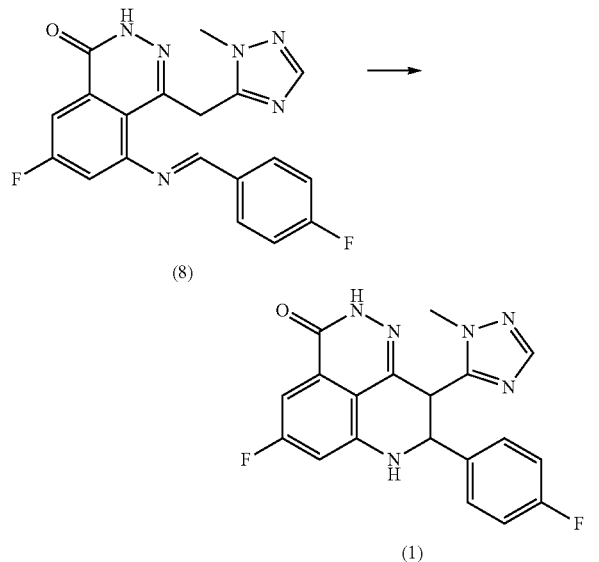

To a suspension of (E)-7-fluoro-5-(4-fluorobenzylideneamino)-4-((1-methyl-1H-1,2,4-triazol-5-yl)methyl)phthalazin-1(2H)-one (8) (2.0 g, 5.3 mmol) in THF (80 mL) was added cesium carbonate (3.4 g, 10.6 mmol). The reaction mixture was stirred at 55° C. for 4 hours and cooled down to room temperature. The mixture was diluted with water (50 ml) and extracted with ethyl acetate (50 mL×3). The combined organic layers were dried over anhydrous Na$_2$SO$_4$ and evaporated to dryness to afford the title compound as a white solid (1.6 g, yield 80%). LC-MS (ESI) m/z: 381 (M+1)$^+$. $^1$H-NMR (400 MHz, DMSO-d$_6$) δ (ppm): 3.66 (s, 3H), 4.97-5.04 (m, 2H), 6.91-6.94 (dd, J$_1$=2.4, J$_2$=11.2 Hz, 1H), 7.06-7.09 (dd, J$_1$=2.4, J$_2$=8.8 Hz, 1H), 7.14-7.18 (m, 3H), 7.47-7.51 (m, 2H), 7.72 (s, 1H), 7.80 (s, 1H), 12.35 (s, 1H).

Example 8

(E)-Methyl 5-fluoro-2-(3-(4-fluorophenyl)-2-(1-methyl-1H-1,2,4-triazol-5-yl)acryloyl)-3-nitrobenzoate (9)

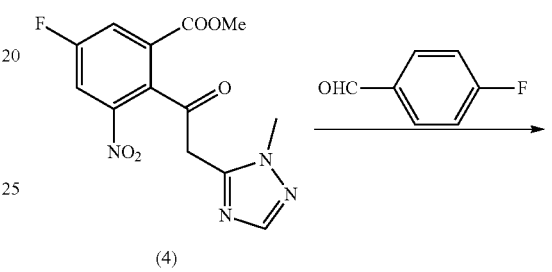

(4)

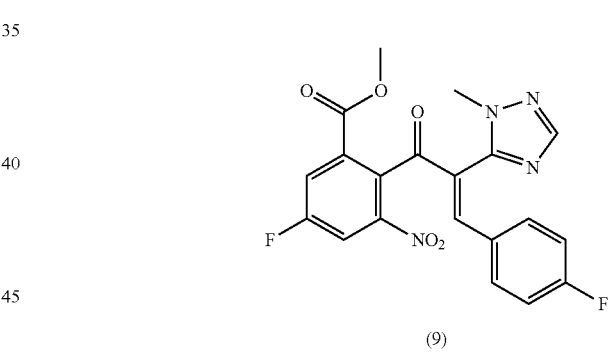

(9)

To a stirred solution of methyl 5-fluoro-2-(2-(1-methyl-1H-1,2,4-triazol-5-yl)acetyl)-3-nitrobenzoate (4) (580 mg, 2 mmol) and 4-fluorobenzaldehyde (488 mg, 4 mmol) in dimethylsulfoxide (2 mL) was added L-proline (230 mg, 2 mmol). The resulting mixture was kept with stirring at 45° C. for 48 hours. The reaction system was then partitioned between ethyl acetate (50 mL) and water (30 mL), and the organic phase was washed with water (20 mL×3), dried with Na$_2$SO$_4$, concentrated in vacuo, and purified by column chromatography (ethyl acetate:petroleum ether=1:3) to give the title compound (9) as a pale yellow foam (340 mg, yield 40%). LC-MS (ESI) m/z: 429 (M+1)$^+$. $^1$H-NMR (400 MHz, DMSO-d$_6$); 6 (ppm): 3.56 (s, 3H), 3.86 (s, 3H), 7.02 (dd, 2H), 7.21 (dd, 2H), 7.90 (s, 1H), 8.08 (s, 1H), 8.26 (dd, 1H), 8.56 (dd, 1H).

Example 9

Methyl 7-fluoro-2-(4-fluorophenyl)-1-hydroxy-3-(1-methyl-1H-1,2,4-triazol-5-yl)-4-oxo-1,2,3,4-tetrahydroquinoline-5-carboxylate (10)

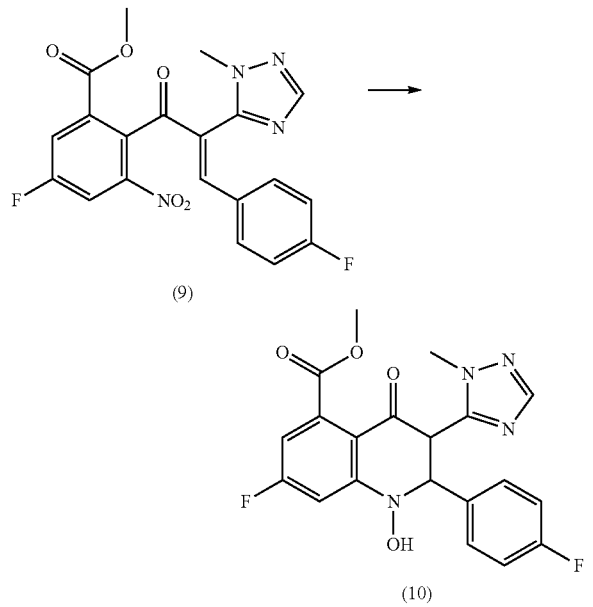

To a solution of (E)-Methyl 5-fluoro-2-(3-(4-fluorophenyl)-2-(1-methyl-1H-1,2,4-triazol-5-yl)acryloyl)-3-nitrobenzoate (9) (200 mg, 0.467 mmol) in methanol (20 mL) was added 10% Pd/C (24 mg). After the addition, the mixture was stirred under H₂ (1 atm) at room temperature for 0.5 h. The reaction system was then filtered and evaporated under reduced pressure. The residue was purified by chromatography (ethyl acetate:petroleum ether=1:1) to give the title compound (10) (110 mg, yield 57%) as an off-white foam. LC-MS (ESI) m/z: 415 (M+H)$^+$. $^1$H-NMR (400 MHz, DMSO-d$_6$) δ (ppm): 3.53 (s, 3H), 3.73 (s, 3H), 5.08 (d, 2H), 5.27 (d, 2H), 6.95 (dd, 1H), 7.08 (dd, 2H), 7.15 (dd, 1H), 7.42 (dd, 2H), 7.77 (s, 1H), 9.92 (s, 1H).

Example 10

Methyl 7-fluoro-2-(4-fluorophenyl)-3-(1-methyl-1H-1,2,4-triazol-5-yl)-4-oxo-1,2,3,4-tetrahydroquinoline-5-carboxylate (5)

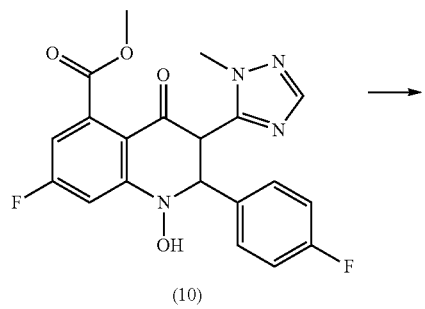

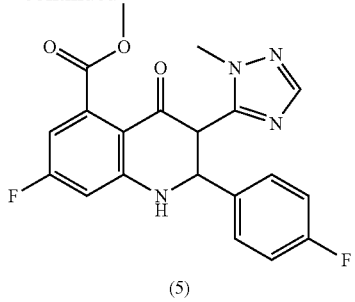

To a stirred solution of methyl 7-fluoro-2-(4-fluorophenyl)-1-hydroxy-3-(1-methyl-1H-1,2,4-triazol-5-yl)-4-oxo-1,2,3,4-tetrahydroquinoline-5-carboxylate (10) (41.4 mg, 0.1 mmol) in methanol (5 mL) was added concentrated HCl solution (w/w 37%, 1 mL) and reductive powdered Fe (56 mg, 1 mmol). The reaction mixture was refluxed for 3 hours. After the disappearance of compound (10) as monitored by LC-MS, the reaction system was partitioned between ethyl acetate (20 mL) and water (20 mL) and then the aqueous phase was extracted with ethyl acetate (10 mL×3). The combined organic phase was dried with Na₂SO₄, concentrated in vacuo and purified by column chromatography (ethyl acetate:petroleum ether=1:1) to give the title compound (5) as a pale yellow solid (12 mg, yield 30%). LC-MS (ESI) m/z: 399 (M+1)$^+$. $^1$H-NMR (400 MHz, CDCl₃) δ (ppm): 3.58 (s, 3H), 3.87 (s, 3H), 4.17 (d, 1H), 4.87 (s, 1H), 5.38 (d, 1H), 6.50 (dd, 2H), 6.99 (dd, 2H), 7.38 (dd, 2H), 7.80 (s, 1H).

Example 11

Methyl 7-fluoro-2-(4-fluorophenyl)-3-(1-methyl-1H-1,2,4-triazol-5-yl)-4-oxo-1,2,3,4-tetrahydroquinoline-5-carboxylate (5)

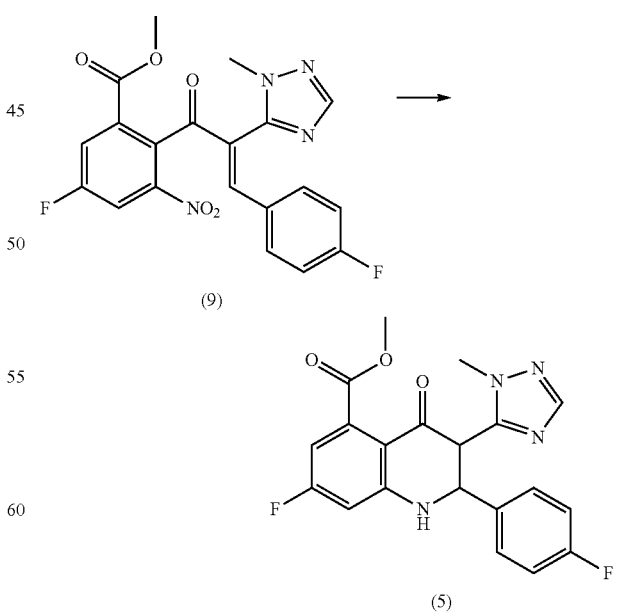

To a solution of (E)-Methyl 5-fluoro-2-(3-(4-fluorophenyl)-2-(1-methyl-1H-1,2,4-triazol-5-yl)acryloyl)-3-nitrobenzoate (9) (214 mg, 0.5 mmol) in methanol (5 mL) was added concentrated HCl solution (w/w 37%, 1 mL), then reductive Fe powder (140 mg, 2.5 mmol) was added slowly to the reaction system. After the addition was complete the resulting mixture was refluxed for 24 hours. The reaction mixture was then filtered, concentrated, neutralized with saturated NaHCO$_3$ (20 mL), and extracted with ethyl acetate (10 mL×3). The residue was purified by chromatography (ethyl acetate:petroleum ether=1:1) to give the title compound (5) (30 mg, yield 15%) as an off-white foam. LC-MS (ESI) m/z: 399 (M+H)$^+$. $^1$H-NMR (400 MHz, DMSO-d$_6$) δ (ppm): 3.56 (s, 3H), 3.86 (s, 3H), 7.02 (dd, 2H), 7.21 (dd, 2H), 7.90 (s, 1H), 8.08 (s, 1H), 8.26 (dd, 1H), 8.56 (dd, 1H).

Example 12

(8R,9S)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (1a) and (8S,9R)-5-fluoro-8-(4-fluorophenyl)-9-(1-methyl-1H-1,2,4-triazol-5-yl)-8,9-dihydro-2H-pyrido[4,3,2-de]phthalazin-3 (7H)-one (1b)

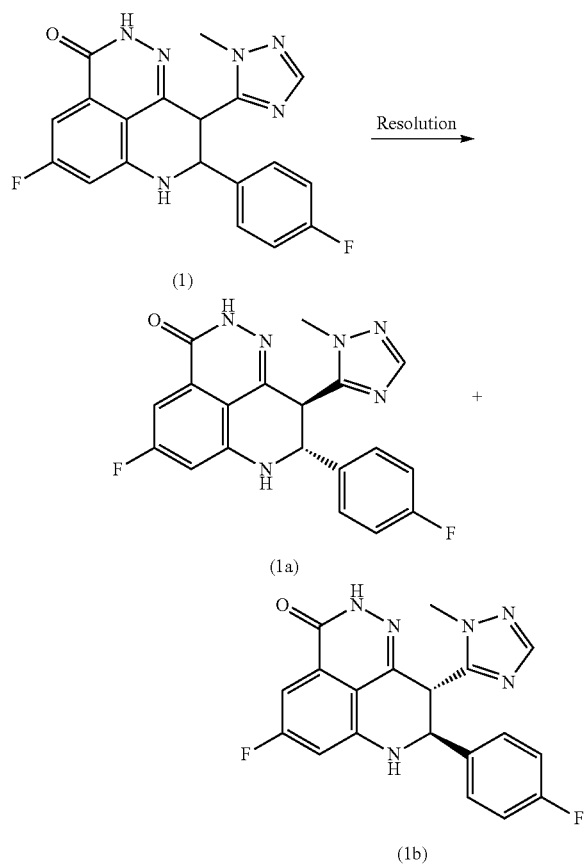 [SMILES: Cn1ncnc1C1c2n[nH]c(=O)c3cc(F)cc(c23)NC1c1ccc(F)cc1 ; Cn1ncnc1[C@@H]1c2n[nH]c(=O)c3cc(F)cc(c23)N[C@H]1c1ccc(F)cc1 ; Cn1ncnc1[C@H]1c2n[nH]c(=O)c3cc(F)cc(c23)N[C@@H]1c1ccc(F)cc1]

A chiral resolution of 5-fluoro-8-(4-fluorophenyl)-9-(1-methyl-1H-1,2,4-triazol-5-yl)-8,9-dihydro-2H-pyrido[4,3,2-de]phthalazin-3(7H)-one (1) (52.5 g) was carried out on a super-fluid chromatography (SFC) unit using a CHIRALPAK IA column and CO$_2$/methanol/diethylamine (80/30/0.1) as a mobile phase. This afforded two enantiomers with retention times of 7.9 minute (23.6 g, recovery 90%, >98% ee) and 9.5 minute (20.4 g, recovery 78%, >98% ee) as analyzed with a CHIRALPAK IA 0.46 cm×15 cm column and CO$_2$/methanol/diethylamine (80/30/0.1) as a mobile phase at a flow rate of 2 g/minute.

Example 13

(2R,3R)-methyl 7-fluoro-2-(4-fluorophenyl)-3-(1-methyl-1H-1,2,4-triazol-5-yl)-4-oxo-1,2,3,4-tetrahydroquinoline-5-carboxylate (6a) and (2S,3S)-methyl 7-fluoro-2-(4-fluorophenyl)-3-(1-methyl-1H-1,2,4-triazol-5-yl)-4-oxo-1,2,3,4-tetrahydroquinoline-5-carboxylate (6b)

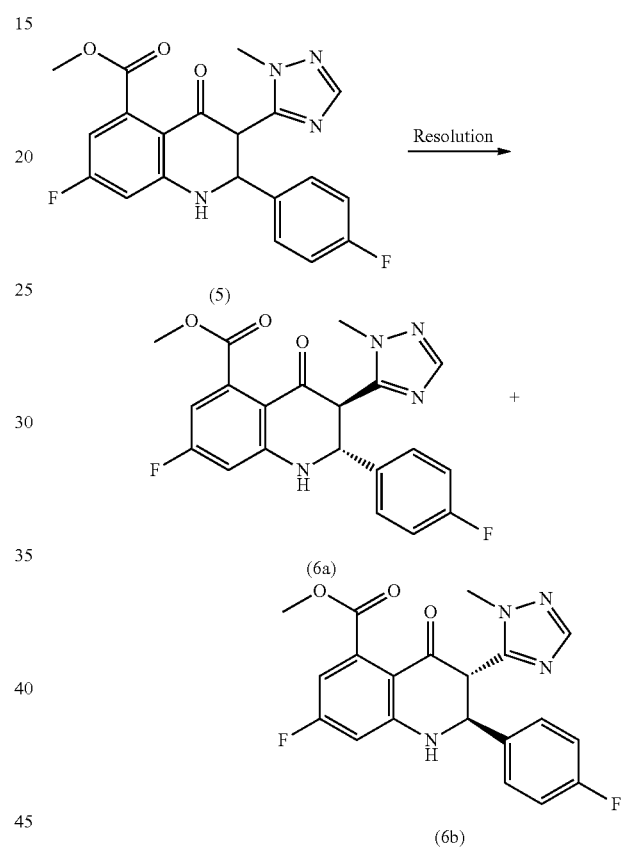

Example 13A

The chiral resolution of compound (5) was carried out on a SFC unit with a CHIRALPAK®IC 3 cm (I.D.)×25 cm, 5 µm column, using CO$_2$/MeOH (80/20) as a mobile phase at a flow rate of 65 g/minute while maintaining the column temperature at 35° C. and with a detection UV wavelength of 254 nm. As such, a racemate of compound (5) (5 g) in methanol solution was resolved, which resulted in two enantiomers with a retention times of 2.35 minute (2.2 g, 88% recovery, >98% ee) and 4.25 minute (2.3 g, 92% recovery, >98% ee), respectively when analyzed using CHIRALPAK®IC 0.46 cm×15 cm column and CO$_2$/MeOH (80/20) as a mobile phase at a flow rate of 2 mL/minute.

Example 13B

The chiral resolution of compound (5) was carried out on a SFC unit with a CHIRALPAK®IC 5 cm (I.D.)×25 cm, 5

μm column, using CO$_2$/MeOH (75/25) as a mobile phase at a flow rate of 200 mL/minute while maintaining the column temperature at 40° C. and with a detection UV wavelength of 255 nm. As such, a racemate of compound (5) (1.25 kg) in methanol solution was resolved, which resulted in two enantiomers in about 83% yield and 97.4% purity.

Example 13C

Alternatively, the separation can also be achieved on a Simulated Moving Bed (SMB) unit with a CHIRALPAK®IC column and acetonitrile as a mobile phase. The retention times for the two enantiomers are 3.3 and 4.1 minutes, respectively. In certain embodiments, the productivity can be greater than 6 kg Feed/day/kg CSP.

Example 14

(8R,9S)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (1a) and (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (1b)

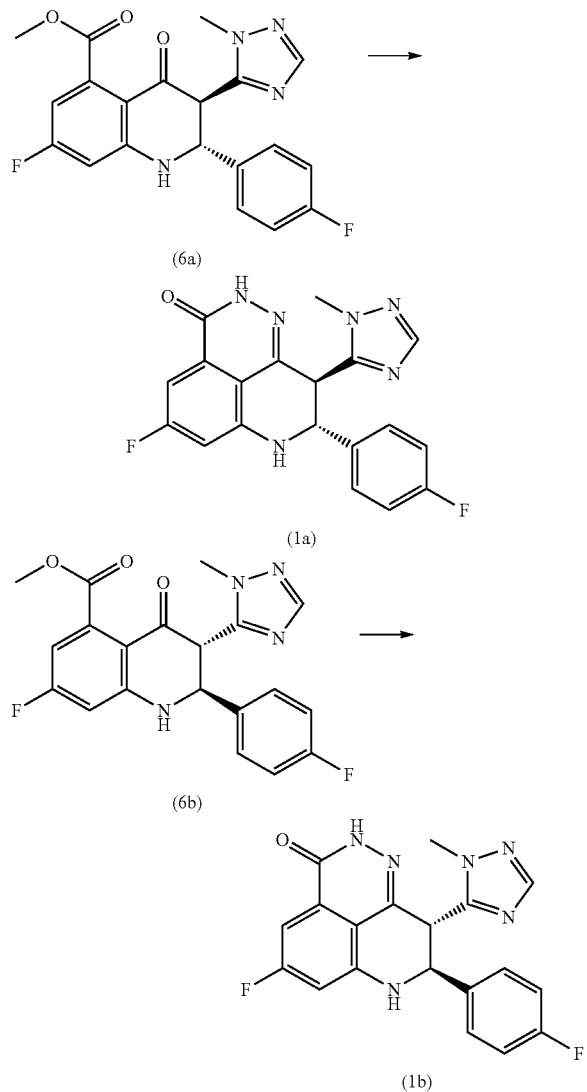

(6a)

(1a)

(6b)

(1b)

Example 14A

To a solution of (2R,3R)-methyl 7-fluoro-2-(4-fluorophenyl)-3-(1-methyl-1H-1,2,4-triazol-5-yl)-4-oxo-1,2,3,4-tetrahydroquinoline-5-carboxylate (6a) or (2S,3S)-methyl 7-fluoro-2-(4-fluorophenyl)-3-(1-methyl-1H-1,2,4-triazol-5-yl)-4-oxo-1,2,3,4-tetrahydroquinoline-5-carboxylate (6b) (400 mg, 1.0 mmol) in ethanol (8.0 mL) was added hydrazine monohydrate (85%, 2.0 mL), and the solution stirred at room temperature for 2 hours. The resulting solution was then concentrated to a volume of 2 mL and filtered, and the resultant cake washed with ethanol (1 mL). After drying in vacuum at 50° C., this afforded the title compound as a white solid (209 mg, yield 55%). LC-MS (ESI) m/z: 381 (M+1)$^+$. $^1$H-NMR (400 MHz, DMSO-d$_6$): δ (ppm): 3.681 (s, 3H), 4.99-5.06 (m, 2H), 6.92-6.96 (m, 1H), 7.08-7.11 (m, 1H), 7.16-7.21 (t, J=8.8 Hz, 2H), 7.49-7.53 (m, 2H), 7.75 (s, 1H), 7.83 (s, 1H), 12.35 (s, 1H).

Example 14B

To a solution of (2R,3R)-methyl 7-fluoro-2-(4-fluorophenyl)-3-(1-methyl-1H-1,2,4-triazol-5-yl)-4-oxo-1,2,3,4-tetrahydroquinoline-5-carboxylate (6a) or (2S,3S)-methyl 7-fluoro-2-(4-fluorophenyl)-3-(1-methyl-1H-1,2,4-triazol-5-yl)-4-oxo-1,2,3,4-tetrahydroquinoline-5-carboxylate (6b) (446 g) in acetonitrile (10 volume) was added hydrazine monohydrate (2.9 eq.), and the solution stirred at room temperature for 2 hours. The resulting solution was then concentrated to a volume of 2 mL and filtered. The crude product was re-slurried with water (3~5 volumes) at 15~16° C. After drying in vacuum at 50° C., this affords the title compound as a white solid (329 g, yield 77%, 99.93% purity). LC-MS (ESI) m/z: 381 (M+1)$^+$; $^1$H-NMR (400 MHz, DMSO-d$_6$) δ (ppm): 3.681 (s, 3H), 4.99-5.06 (m, 2H), 6.92-6.96 (m, 1H), 7.08-7.11 (m, 1H), 7.16-7.21 (t, J=8.8 Hz, 2H), 7.49-7.53 (m, 2H), 7.75 (s, 1H), 7.83 (s, 1H), 12.35 (s, 1H).

A number of embodiments have been described herein. It should be understood, however, that various modifications may be made without departing from the spirit and scope of the present invention. Accordingly, other embodiments are within the scope of the following claims.

What is claimed is:

1. A compound of formula (A):

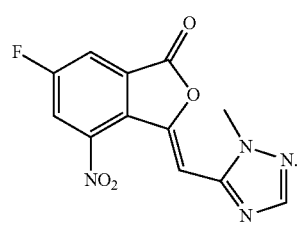

(A)

* * * * *